United States Patent

Hsi Ho et al.

[11] Patent Number: 6,071,864
[45] Date of Patent: Jun. 6, 2000

[54] METHODS FOR PREPARATION OF ARYLATED POLY OLEFINS

[75] Inventors: Suzzy Chen Hsi Ho, Dayton; Margaret May-Som Wu, Skillman, both of N.J.

[73] Assignee: Mobil Oil Corporation, Fairfax, Va.

[21] Appl. No.: 09/118,353

[22] Filed: Jul. 17, 1998

[51] Int. Cl.[7] .................................... C07C 2/66
[52] U.S. Cl. ....................... 508/591; 585/24; 585/326; 585/329; 585/467
[58] Field of Search ................. 585/24, 326, 329; 508/591

[56] References Cited

U.S. PATENT DOCUMENTS

| | | |
|---|---|---|
| 3,742,082 | 6/1973 | Brennan .................... 260/683.9 |
| 4,219,686 | 8/1980 | Petrillo et al. ................ 585/24 |
| 4,537,696 | 8/1985 | Beimesch .................... 252/75 |
| 4,992,183 | 2/1991 | Beimesch et al. ............ 252/32.7 |
| 5,008,460 | 4/1991 | Garwood et al. .............. 585/24 |
| 5,019,670 | 5/1991 | Le et al. ...................... 585/24 |
| 5,107,049 | 4/1992 | Le et al. ...................... 585/24 |
| 5,132,477 | 7/1992 | Ho et al. ...................... 585/24 |
| 5,254,274 | 10/1993 | Ho et al. ..................... 585/24 |

OTHER PUBLICATIONS

Shubkin, R.L. (ed.), "Synthetic Lubricants and High–Performance Functional Fluids", Marcel Deker, Inc., New York, 1993.

*Primary Examiner*—Ellen M. McAvoy

[57] ABSTRACT

Novel methods for the preparation of modified poly α-olefins, and compositions prepared by the novel methods are disclosed. The modified poly alpha-olefins of the present invention are useful as base fluids or additives in synthetic lubricants.

10 Claims, 3 Drawing Sheets

C12 TO C24, FOLLOWED BY TOLUENE ADDITION

METHODS FOR PREPARATION OF ARYLATED POLY OLEFINS

FIELD OF THE INVENTION

The present invention relates to novel methods for the preparation of arylated poly α-olefins and compositions prepared by the methods. The poly alpha-olefins of the present invention are useful as synthetic lubricants.

BACKGROUND OF THE INVENTION

Poly α-olefins (PAOs) are known to be useful as synthetic lubricants. PAO base stocks are typically prepared by polymerization of α-olefins, followed by hydrogenation to remove residual unsaturation. The polymerization of the α-olefins is usually performed in the presence of a Lewis Acid catalyst such as boron trifluoride or aluminum chloride, in complex with a promoter such as water, an alcohol, an ester, or an acid. See for example U.S. Pat. No. 3,742,082 to Brennan.

Typically, a polar ester base stock is added to PAO base stocks to improve additive or sludge solvency, volatility and/or seal swell characteristics. However, these polar esters suffer from the disadvantages of being hydrolyzable in the presence of water, and of having thermal and oxidative stabilities that are inferior to PAOs.

However, esters involve relatively expensive material costs and complicated production processes. A lower cost additive would be greatly desired.

Alkylbenzene base stocks are known in the art. See "Synthetic Lubricants and High-Performance Functional Fluids", Shubkin, R. L., Ed., Marcel Deker, Inc., New York 1993. However, alkylbenzene base stocks have not been used extensively in lubricant formulations because they are produced as an undesirable side-product in the production of detergent alkylates, and thus both their supply and their quality are unreliable.

Arylated PAO base stock synthetic lubricants are known to improve hydrolytic and thermal oxidative properties as compared to esters. However, until now, their preparation has been fraught with difficulties which resulted in low yields and poor, unreliable quality.

In the past, olefins and aromatic compounds were reacted in a single reaction step to provide an intermediate monoalkylbenzene. See P. R. Pujado, Linear Alkylbenzene (LAB) Manufacture, Chapter 1.5.; Handbook of Petroleum Refining Processes, 2nd Ed., Editor—Robert A. Meyers, McGraw Hill, N.Y. 1977. While monoalkylates are useful for detergent alkylate, they are not suitable for lube stock because these detergent alkylates are usually made from benzene alkylation with $C_{10}$ to $C_{16}$ olefins, and their total molecular weight range only from 218 ($C_{10}$–$B_z$) to 302 ($C_{16}$–$B_z$). Some typical commercial LAB fluids have boiling ranges of from about 553 to about 580° F., and their 100° C. viscosities are usually less than 3.0 cS. These LAB are too volatile, and possess viscosities that are too low for high quality lube applications. Thus, in order to produce a suitable lube stock with very low volatility and a wide range of viscosities to provide adequate lubricity, a second alkylation step is required, which results in decreased yield.

Another advantage of this invention is that the fluid described here has properties superior to a simple PAO fluid. PAOs are currently produced from polymerization of α-olefins followed by hydrogenation to remove unsaturated double bonds, to produce a finished PAO base stock. The finished base stock is purely a paraffinic fluid, and therefore has very poor additive or sludge solvency and dispersancy. In most synthetic lubricant PAO formulations, an ester is used as co-basestock to improve the solvency and dispersancy of PAO base fluid. By adding an aromatic component to the PAO structure, one can significantly improve solvency and dispersancy, allowing the formulation of synthetic products without using an added ester, thus eliminating the problem associated with ester fluid, such as poor hydrolytic stability.

Accordingly, improved arylated poly α-olefins and methods for their preparation are needed. This invention is directed to this important end.

SUMMARY OF THE INVENTION

In accordance with the present invention, methods are provided for the preparation of arylated poly α-olefins comprising the steps of:

(a) oligomerizing one or more α-olefins to form olefin dimers and some higher oligomers; and (b) arylating the olefin oligomers with an aromatic compound to form the arylated poly α-olefin.

In some preferred embodiments of the methods of the invention, the oligomerization of the α-olefins and the arylation of the olefin oligomers are performed in the presence of an acid catalyst. Preferably, the catalyst is a promoted catalyst Lewis Acid catalyst. More preferably, the catalyst is selected from $BF_3$, $AlCl_3$, triflic acid, $BCl_3$, $AlBr_3$, $SnCl_4$, $GaCl_3$ and an acid clay catalyst.

In further preferred embodiments of the methods of the invention the α-olefins have from about 6 to about 20 carbon atoms, preferably from about 8 to about 16 carbon atoms, more preferably from about 10 to about 14 carbon atoms, and even more preferably from about 10 to about 12 carbon atoms.

In some preferred embodiments the olefin dimers have from about 16 to about 30 carbon atoms.

Preferably, the aromatic compound is benzene, naphthalene, furan, thiophene, anthracene, phenanthrene, pyrole, indole, benzothiophene, dibenzothiophene, benzofuran, dibenzofuran, phenoxathiin, thianthrene, biphenyl or pyrene, each of which can be optionally substituted.

In further preferred embodiments, the aromatic compound is toluene, 0-, — or p-xylene, hydroxybenzene, alkoxybenzene such as methoxy or ethoxybenzene, thioanisole, diphenylether, diphenylmethane, bisphenol-A, bisphenol sulfide, diphenyl sulfide, naphthalene, methylnaphthalene, methoxynaphthalene, ethoxynaphthalene, methylnaphthal sulfide, ethyl naphthylsulfide, or a mixture thereof.

In more preferred embodiments the aromatic compound is an optionally substituted benzene or an optionally substituted naphthalene.

Also provided in accordance with the present invention are novel arylated poly α-olefin compositions produced by the methods of the invention.

DETAILED DESCRIPTION OF THE PREFERRED EMBODIMENTS

Figure 1A:
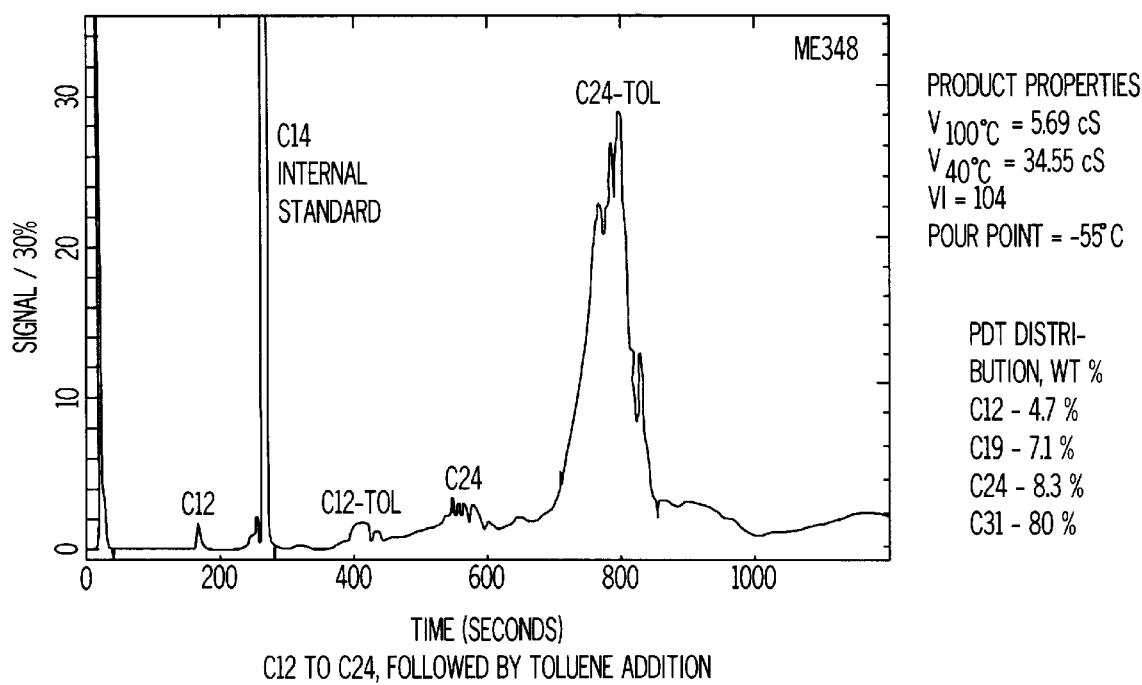
FIG. 1A and FIG. 1B are gas chromatograms of the products of Ar-PAO synthesis by the methods of the present invention, and by conventional di-alkylbenzene synthesis.

The present invention is directed to novel methods for the preparation of arylated poly α-olefins (Ar-PAO). The arylated poly α-olefins of the present invention possess excellent viscometric, hydrolytic, thermal and oxidative stabilities. They also possess excellent additive solvencies, and can be prepared in high quality, and with high yield.

The products of the methods of the invention are useful as substitutes for polar ester base stock additives in industrial or engine oil formulations. The arylated poly α-olefins prepared in accordance with the present invention also can be used as fuel additives to enhance properties of the fuel.

According to the present invention, methods for the preparation of arylated poly α-olefins are provided comprising the steps of:

(a) oligomerizing one or more α-olefins to form olefin dimers and some higher oligomers; and (b) arylating the olefin oligomers with an aromatic compound to form the arylated poly α-olefins.

The methods of the present invention are represented in Scheme I, below:

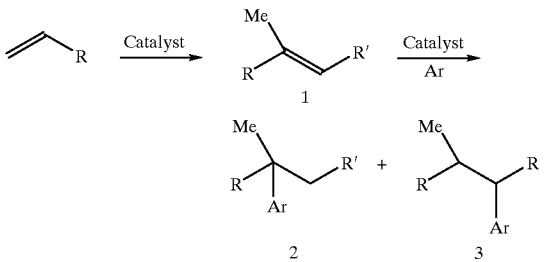

wherein R and R' are optionally substituted alkyl groups and Ar is an optionally substituted aryl compound.

In accordance with the present invention, an α-olefin is oligomerized in the presence of promoted catalyst to give predominantly olefin dimer and higher oligomers(1). Once the reaction has gone to completion, an aromatic composition containing one or more aromatic compounds is reacted with the oligomers, in the presence of the same catalyst, to give aromatic α-olefins (2) and (3) in high yield.

In preferred embodiments, the α-olefin has from 6 to about 20 carbon atoms. In more preferred embodiments, the α-olefin has from about 8 to about 16 carbon atoms. In especially preferred embodiments the α-olefin has from about 8 to about 14 carbon atoms.

In accordance with the present invention, one or more α-olefins are oligomerized to form predominantly olefin dimer, with some trimer or higher oligomers. In preferred embodiments the olefin dimer has from about 20 to about 36 carbon atoms, more preferably from about 20 to about 28 carbon atoms.

In accordance with preferred embodiments of the methods of the present invention, the α-olefin dimers and higher oligomers are arylated with an aromatic compound. A wide variety of aromatic compounds are suitable for use in the methods of the present invention. Suitable aromatic compounds include, but are not limited to, substituted or unsubstituted benzene, substituted or unsubstituted naphthalene, substituted or unsubstituted furan, substituted or unsubstituted thiophene, substituted or unsubstituted anthracene, substituted or unsubstituted phenanthrene, substituted or unsubstituted pyrole, substituted or unsubstituted indole, substituted or unsubstituted benzothiophene, substituted or unsubstituted dibenzothiophene, substituted or unsubstituted benzofuran, substituted or unsubstituted dibenzofuran, substituted or unsubstituted phenoxanthiin, substituted or unsubstituted thianthrene, substituted or unsubstituted biphenyl, substituted or unsubstituted pyrene, bisphenol A, bisphenol sulfide, anisole, thioanisole, diphenyl oxide, diphenyl sulfide, diphenylmethane, and their substituted analogs. In more preferred embodiments the aromatic compound is an optionally substituted benzene or an optionally substituted naphthalene.

In further preferred embodiments, the aromatic compound is toluene, 0-, — or p-xylene, hydroxybenzene, alkoxybenzene such as methoxy or ethoxybenzene, thioanisole, diphenylether, diphenylmethane, diphenyl sulfide, naphthalene, methylnaphthalene, methoxyhaphthalene, ethoxynaphthalene, methylnaphthal sulfide, ethyl naphthylsulfide, bisphenol-A, bisphenol sulfide or a mixture thereof.

The aromatic compound can be substituted. Suitable substituent groups include alkyl, hydroxy, alkoxy such as methoxy or ethoxy, aroxy such as phenoxy, alkylthio such as methanethio, arylthio such as phenylthio, and aralkyl such as benzyl. Thus, in some preferred embodiments the aromatic compound is a mono-substituted benzene, for example toluene, or a disubstituted benzene, for example para-, meta- or ortho-xylene.

As used herein, the term "alkyl" includes straight-chain, branched and cyclic hydrocarbon groups. Examples of alkyl groups include methyl, ethyl, propyl, isopropyl, decanyl, dodecyl, and tetradecanyl groups.

As used herein, the term "arylated" refers to the reaction of the olefin dimer and oligomers with the aromatic compound to form the products described herein. As used herein, the term "α-olefin" denotes an olefin containing unsaturation (i.e., a carbon-carbon double bond) in the 1-position.

In some preferred embodiments, the catalysts used in accordance with the methods of the present invention include a Lewis acid catalyst such as $BF_3$, $AlCl_3$, triflic acid, $BCl_3$, $AlBr_3$, $SnCl_4$, $GaCl_3$, an acid clay catalyst, or an acidic zeolite, for example zeolite Beta, USY, Mordenite, Montmorillonite, or other acidic layered, open-structure zeolites, such as MCM-22, MCM-56 or solid superacids, such as sulfated zirconia, and activated $Wo_x/ZrO_2$. In particularly preferred embodiments, the catalyst is $BF_3$ or $AlCl_3$.

A preferred catalyst for use in the present invention is MCM-56. MCM-56 is a member of the MCM-22 group useful in the invention which includes MCM-22, MCM-36, MCM-49 and MCM-56. MCM-22 is described in U.S. Pat. No. 4,954,325. MCM-36 is described in U.S. Pat. No. 5,250,277 and MCM-36 (bound) is described in U.S. Pat. No. 5,292,698. MCM-49 is described in U.S. Pat. No. 5,236,575 and MCM-56 is described in U.S. Pat. No. 5,362,697.

The catalysts as mixed metal oxide super acids comprise an oxide of a Group IVB metal, preferably zirconia or titania. The Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The combination of Group IVB metal oxide with an oxyanion of a Group VIB metal is believed to enter into an actual chemical interaction which, in any event, provides a composition with more acidity than a simple mixture of separately formed Group IVB metal oxide mixed with a separately formed Group VIB metal oxide or oxyanion.

The acidic solid materials useful as a catalyst in the present process are described in U.S. Pat. Nos. 5,510,539 and 5,563,310. These solid materials comprise an oxide of a Group IVB metal, preferably zirconia or titania. The Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in Proceeding 9th International Congress on Catalysis, Volume 4, pages 1727–1735 (1988). According to these publications, tungstate is impregnated onto a preformed solid zirconia material. This chemical interaction is discussed in the aforementioned article by K. Arata and M. Hino which also suggests that solid superacids are formed when sulfates are reacted with hydroxides or oxides of certain metals, e.g., Zr. These superacids are said to have the structure of a bidentate sulfate ion coordinated to the metal, e.g., Zr. The article suggests further that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure. It is further suggested that the tungsten oxide combines with zirconium oxide compounds to create superacid sites at the time the tetragonal phase is formed.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Suitable sources of the Group IVB metal oxide, used for preparing the catalyst, include compounds capable of generating such oxides, such as oxychlorides, chlorides, nitrates, oxynitrates, etc., particularly of zirconium or titanium. Alkoxides of such metals may also be used as precursors or sources of the Group IVB metal oxides. Examples of such alkoxides include zirconium n-propoxide and titanium i-propoxide. These sources of a Group IVB metal oxide, particularly zirconia, may form zirconium hydroxide, i.e., $Zr(OH)_4$, or hydrated zirconia as intermediate species upon precipitation from an aqueous medium in the absence of a reactive source of tungstate. The expression, hydrated zirconia, is intended to connote materials comprising zirconium atoms covalently linked to other zirconium atoms via bridging oxygen atoms, i.e., Zr—O—Zr., further comprising available surface hydroxy groups. When hydrated zirconia is impregnated with a suitable source of tungstate under sufficient conditions, these available surface hydroxyl groups are believed to react with the source of tungstate to form an acidic catalyst. As suggested in the article by K. Arata and M. Hino, precalcination of $Zr(OH)_4$ at a temperature of from about 100° C. to about 400° C. results in a species which interacts more favorably with tungstate upon impregnation therewith. This precalcination is believed to result in the condensation of ZrOH groups to form a polymeric zirconia species with surface hydroxyl groups which may be referred to as a form of a hydrated zirconia.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

It is known that catalysts such as those described herein are advantageously employed in conjunction with a promoter. Suitable promoters for use with the catalysts in the present invention include those known in the art, for example water, alcohols, or esters, or acids.

In preferred embodiments of the methods of the present invention, the ratio of aromatic compound to α-olefin oligomers is from about 0.5:1 to about 20:1. In more preferred embodiments the ratio of aromatic compound to α-olefin oligomers is from about 0.1:1 to about 8:1.

The methods of the present invention provide arylated poly α-olefins in higher yield than the conventional alkylbenzene fluid synthesis, where 2 moles of α-olefin and one mole of aromatic compound are mixed together with a catalyst. Additionally, the composition of the product of the methods of the present invention also differs from the products of the conventional process. Thus, the present invention also provides novel Ar-PAO compositions.

The following examples are illustrative, but are not to be considered limiting of the present invention.

EXAMPLES

General Synthesis of Ar-PAO

In the following examples, the production of Ar-PAO was carried out in a 600 cc Monel autoclave. At the beginning of the reaction, the proper amount of 1-olefin and catalyst promoter were charged into the autoclave and heated to reaction temperature, ~20–100° C. When the temperature stabilized, $BF_3$ gas was fed into the reaction mixture through a dip tube and $BF_3$ pressure was maintained at ~5–100 psi. The reaction mixture was stirred for 1–16 hours until most of the 1-olefin was converted. At this time, benzene, toluene or other aromatics were purged into the autoclave through an Isco pump. The mixture was then stirred overnight. The reaction mixture was then quenched with dilute base solution, washed with water and dried over sodium sulfate. The lube product was isolated by distillation at 150° C. and ~50 millitorr vacuum.

Examples 1 and 2

Comparison of Ar-PAO Synthesis vs. Conventional Alkylbenzene Synthesis

Example 1. Ar-PAO was produced from 1-dodecene with toluene following the procedure described above. The product yields, product distribution and product properties are summarized in FIG. 1A. The lube yield in this run was 80%.

Example 2 (Comparative Example). The product in this example was produced by conventional alkylbenzene fluid synthesis. A 600 cc Monel Autoclave was cleaned with water followed by propanol solvent and dried in a 90° C. oven for one hour. The autoclave was charged with 200 g of 1-dodecene (1.2 mole, from Aldrich Chem. Co., Milwaukee, Wis.), 60 g toluene (0.60 mole) and promoters. The autoclave was purged with $N_2$ to remove any residual air. The reaction mixture was heated to 50° C. with slow agitation. The autoclave was then pressurized with $BF_3$ gas (introduced through a dip tube) to ~25 psi. After 18 hours of stirring, the autoclave was cooled to room temperature, vented, and purged with $N_2$ for one hour to remove most of the dissolved $BF_3$ gas. The reaction mixture was then transferred to a flask containing 300 cc of 5 wt. % NaOH solution with constant stirring. The organic layer was then separated and dried by anhydrous sodium sulfate. The dried organic layer was then distilled on a Rotavap to remove the low boiling toluene. The remaining liquid was further distilled on a high vacuum, short-path distillation apparatus at ~100° C./<1 millitorr to separate $C_{12}$-toluene from $(C_{12})_2$-toluene.

Figure 1B:
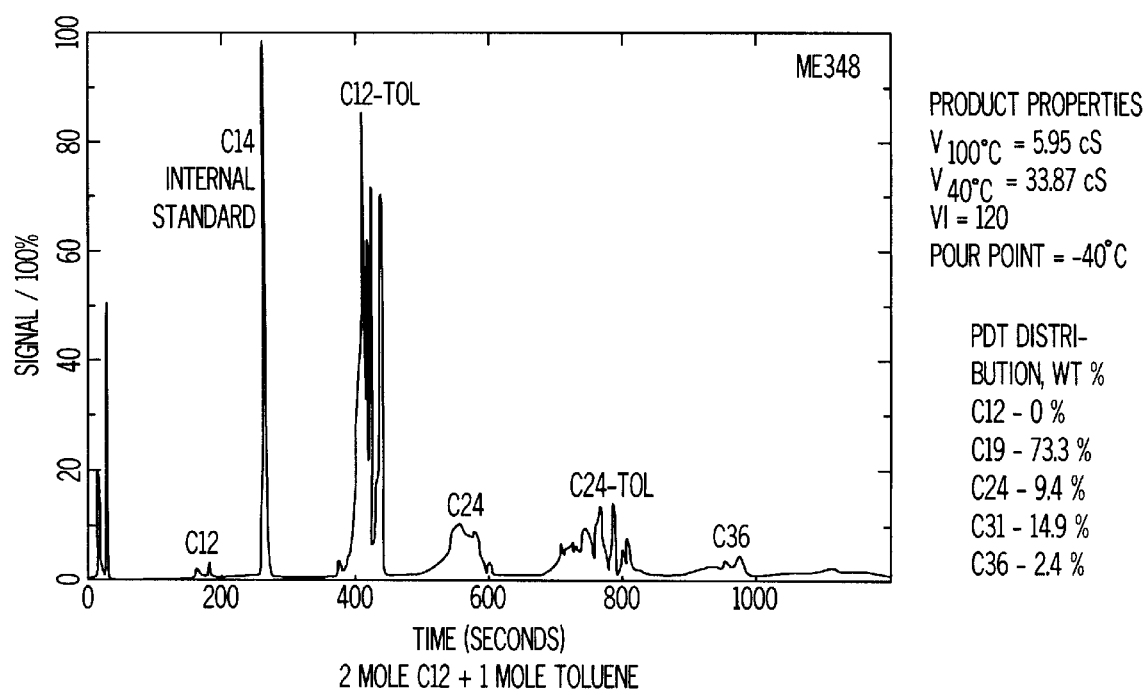
Figure 2:
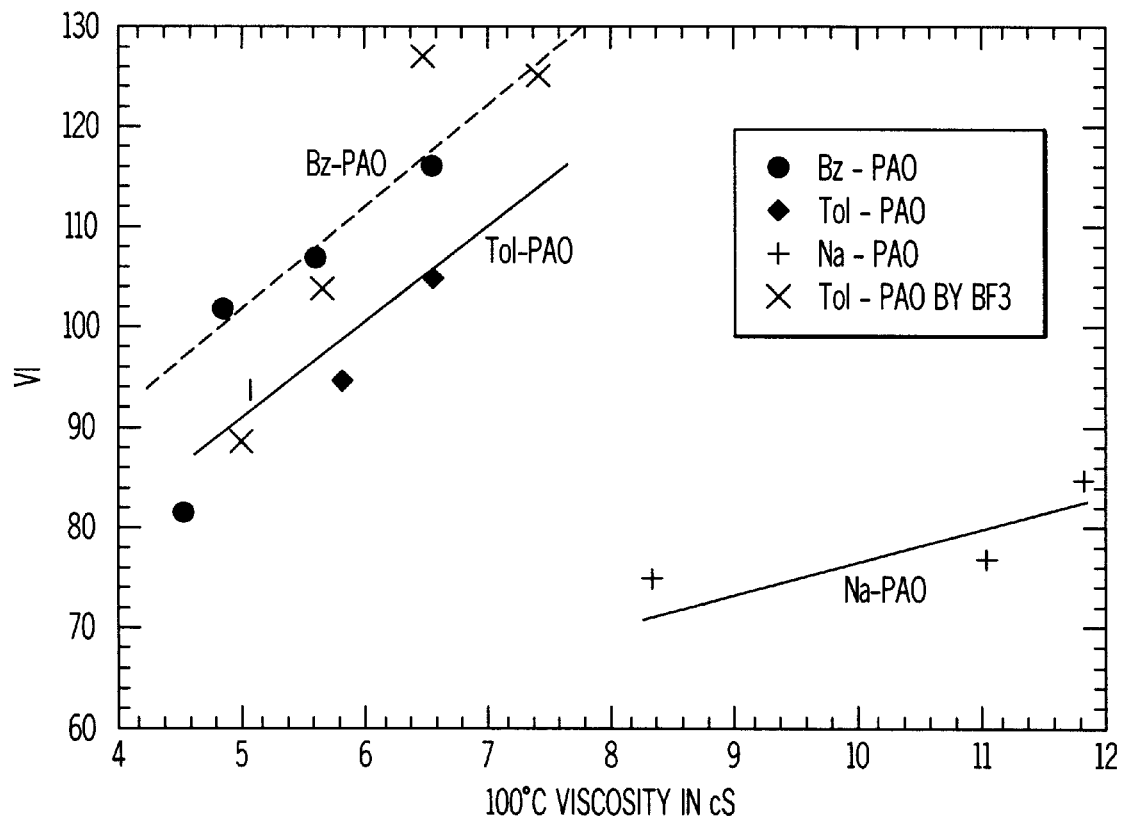
FIG. 2 is a plot of Viscosity Index versus Viscosity for Ar-PAOs listed in Tables 9 and 10.

The product yields, distribution and properties were summarized in FIG. 1B. The lube yield in this run was only 26%. The main product was dodecyltoluene, which is too light and volatile for use as lubricant base stock. Examples 1 and 2 demonstrate that the novel Ar—PAO process described herein produced a lube yield much higher than that of the conventional aklylbenzene process.

Example 3

Comparison of Properties of Ar-PAO

Ar-PAO was produced in 86% yield in accordance with the procedure of Example 1. The properties of the product are summarized in Table 1, together with properties of an ester and PAO fluid.

TABLE 1

Properties Comparison of Ar-PAO vs. Ester and PAO

| Example | 3 | | |
|---|---|---|---|
| Base Stock Type | Tol-PAO | Dibasic Ester (a) | PAO (a) |
| V100° C., cS | 5.97 | 5.2 | 5.6 |
| Viscosity Index (VI) | 105 | 132 | 135 |
| Pour Point, | <-40 | -59 | -62 |
| Oxidative Stability: B10 @ 320° F./40 hrs: (b) | | | |
| % Visc Inc. | 69 | 102 | 64 |
| TAN (b) | 13 | 31 | 17 |
| Sludge | nil | moderate | light |

(a) The dibasic ester is available from Mobil Chemical Co. as DB51. The PAO fluid was available from Mobil Chemical Co. as SHF61.
(b) The B10 oxidation test was conducted by purging air through the oil in the presence of metal catalysts at 3200 for 40 hours and measuring the oil/viscosity increase, total acid number (TAN) change and deposit level.

It can be seen from Table 1 that compared to a dibasic ester, the Ar-PAO has better oxidative stability by B10 test, and better hydrolytic stability as shown by the lower TAN increase. Although not wishing to be bound by any theory, it is believed that Ar-PAO has improved hydrolytic stability because it does not contain a hydrolyzable functional group.

Examples 4 to 6

Properties of Ar-PAO Derived from 1-Decene, 1 Tetradecene and 1-Hexadecene

In these Examples, 1-decene, 1 tetradecene and 1-hexadecene were employed as the starting olefins in the process described in Example 1. The resulting Ar-PAO yields and product properties are summarized in Table 2.

TABLE 2

Ar-PAO Produced from Toluene and α-Olefins of C10 to C16

| Example | 4 | 1 | 5 | 6 |
|---|---|---|---|---|
| α-Olefins | 1-Decene | 1-Dodecene | 1-Tetradecene | 1-Hexadecene |
| Lube Yield, Wt % | 87.2 | 87.4 | — | 92.2 |
| Lube Properties: | | | | |
| V100° C., cS | 4.99 | 5.69 | 6.51 | 7.45 |
| V40° C., cS | 29.71 | 34.55 | 37.57 | 46.38 |
| VI | 89 | 104 | 127 | 125 |
| Pour Point, ° C. | <-55 | -55 | -30 | -21 |

It can be seen from Table 2 that the yields for Ar-PAO remain high for all runs (87–92%). Additionally, lube viscosities of Ar-PAO range from 5 to 7.5 cS, and lube VI increases from 89 to 125. The pour point also increased from <-55° C. to -21° C.

Examples 7 to 10

Properties of Ar-PAO Derived from Benzene, Xylenes or Naphthalene

Other types of aromatic compounds (benzene, xylenes or naphthalene) were used to produce Ar-PAO. The product yields and product properties were summarized in Table 3.

TABLE 3

Synthesis and Properties of Ar-PAO from Benzene, Xylene or Naphthalene with 1-Dodecene

| Example | 7 | 8 | 9 | 10 |
|---|---|---|---|---|
| Olefins | C12 | C12 | C12 | C12 |
| Aromatic Type | Benzene | m-Xylene | o,m,p-Xylene | Naphthalene |
| Olefin/Tol Molar Ratio | 1.1/1 | 1/1 | 1/1.1 | 2/1 |
| Lube Yield, Wt % | 67° | ~70 | ~60 | 94.3 |
| Lube Properties: | | | | |
| V100, cS | 4.99 | 5.97 | 6.70 | 5.69 |
| V40, cS | 29.71 | 36.96 | 46.67 | 34.55 |
| VI | 89 | 105 | 95 | 104 |
| Pour Point, ° C. | | <-40 | — | -55 |

It can be seen from Table 3 that naphthalene has excellent activity and produces more than 90% lube yield. At the end of the reaction, very little naphthalene was left in the mixture. The product also has excellent VI and pour point, and a bromine number of <1. Separate experiments showed that this product has excellent oxidative stability.

The product properties of xylene-PAO are similar to toluene-PAO, with excellent VI and pour point. The use of xylene is thought to be advantageous compared to toluene because it has a higher boiling point, and lower vapor pressure. Generally, meta-xylene or xylene mixtures have lower reactivity than toluene, and produce slightly lower lube yields (60–70%). Ortho-xylene was observed to be most reactive, with 50% conversion, vs. 12.8% conversion for meta-xylene and 7.8% for para-xylene.

Examples 11 to 14

Properties of Ar-PAO Derived Using $AlCl_3$ Catalyst

Ar-PAOs were made by similar procedures as Example 1, except the catalyst used in the reaction was $AlCl_3$ and the aromatic compounds used were toluene and naphthalene. The reaction yields and lube product properties were summarized in Table 4.

TABLE 4

Synthesis of Ar-PAO by AlCl₃ Catalyst

| Example | 11 | 12 | 13 | 14 |
|---|---|---|---|---|
| | Tol-C10PAO | Naph-C10PAO | Tol-C12PAO | Naph-C12PAO |
| Temp, °C. | 120.00 | 80.00 | 45.00 | 45.00 |
| Ar/C10 ratio | 1.2/1 | 0.25/1 | 1.2/1 | 0.21/1 |
| Conv, Wt % | 99.07 | 98.78 | 98.87 | 100.00 |
| Lube Yield, wt | 90.39 | 85.81 | 95.56 | 99.16 |
| Lube Product Properties: | | | | |
| V100° C., cS | 10.36 | 17.24 | 29.77 | 40.11 |
| VI | 117.00 | 126.00 | 146.00 | 142.00 |
| Pour Point, °C. | −52.00 | −48.00 | −40 | −37.00 |
| Bromine No. | 1.50 | 1.70 | 0.8 | 0.30 |

It can be sen from Table 4 that AlCl₃ can be used as catalyst to produce high viscosity, high quality Ar-PAO for use in synthetic lubricant formulation.

Examples 15 and 16

Preparation of Ar-PAO by a Two-stage Process

Ar-PAO can also be prepared in a two stage process. In this process, a PAO was first prepared in a typical polymerization process as shown in Example 1, using $BF_3$ or $AlCl_3$ catalyst. When the polymerization was completed, the olefin dimer and higher oligomers were isolated by distillation to remove any unreacted mono-olefins. The PAO was then separately alkylated by an aromatic compound over $BF_3$, $AlCl_3$, or another acid catalyst, including $Wo_x/ZrO_2$, acid clay, MCM-22 or MCM-56 type catalyst.

Products were prepared from a PAO fraction containing mostly 1-tetradecene dimer (C28 olefin) and benzene or toluene over <1 wt % AlCl₃ catalyst. The product properties and comparisons with typical ester and PAO fluids were summarized in Table 5.

TABLE 5

Reaction Conditions and Properties of Ar-PAO from 1-Tetradecene Dimer and Benzene or Toluene

| Example | 15 | 16 | | |
|---|---|---|---|---|
| | Benzene-C28 | Toluene-C28 | Dibasic ester | PAO |
| Mole ratio, Ar/C28 = | 8/1 | 8/1 | — | — |
| Wt% AlCl3 | 0.8 | 9.7 | — | — |
| Lube Yields, wt % | 95 | 92 | — | — |
| 100° Visc, cS | 6.58 | 7.00 | 5.20 | 5.6 |
| VI | 116 | 108 | 132 | 135 |
| Pour Point, °C. | <−40 | <−40 | −−59 | −62 |
| Oxidative stability: | | | | |
| B10/325° F., 40 hrs | | | | |
| % Visc. Increase | 52 | 70 | 102 | 61 |
| Sludge | light | light | moderate | light |
| DSC induction time, minutes(a) | 55 | 52 | 25 | 36 |

TABLE 5-continued

Reaction Conditions and Properties of Ar-PAO from 1-Tetradecene Dimer and Benzene or Toluene

| Example | 15 | 16 | | |
|---|---|---|---|---|
| Thermal Stability(b) | | | | |
| % loss of 100° C. Visc | — | 4.6 | 26.7 | — |
| Nocack Volatility, wt % | 3.9 | 3.8 | 7.0 | 8.0 |

(a) at 165° C. and 500 psi $O_2$ pressure
(b) Cracking at 300° C. under $N_2$ for 24 hours It can be seen from Table 5 that benzene-$C_{28}$ and toluene-$C_{28}$ have excellent viscometrics (6.6–7 cS, 108–116 VI and <−40° C. pour points). Ar-PAO also showed oxidative stability superior to the dibasic ester by the B10 test or by DSC (differential scanning calorimetry). In the B10 oxidation test, the viscosity increases for Ar-PAOs were 50–70% versus 102% viscosity increase for the esters. The neat Ar-PAO had very similar oxidative stability as a typical Stock 509 PAO.

Ar-PAO also had thermal stability superior to the dibasic ester MCP121—4.6% viscosity loss vs. 26% viscosity loss at 300° C./24 hours.

The Ar-PAO also had excellent Noack volatility. The Ar-PAO prepared from benzene or toluene with $C_{28}$ tetracene dimer has very low volatility, 3.9 and 3.8% Noack volatility, compared to 7% and 8% Noack volatility for the dibasic ester and PAO.

The toluene-$C_{28}$ fluid was used in a synthetic oil formulation (Table 7). The resulting lubricant was clear and had excellent viscometrics and oxidative stability (by the B10 test).

Examples 17 to 21

Preparation of Ar-PAO Using Mixed-α-olefins

In these Examples, the dimer and some trimers of mixed 1-octane, 1-decene and 1-dodecene were reacted with different aromatics according to the procedure in Example 1 to give Ar-PAO having excellent yields and properties. The results are summarized in Table 6.

TABLE 6

Ar-PAO from Dimers of Mixed 1-C8, C10 and C12 Olefins with Aromatics

| Example | 17 | 18 | 19 | 20 | 21 |
|---|---|---|---|---|---|
| Aromatics | Bz | Tol | toluene | xylene | Naphthalene |
| Molar Ratio Aromatic/Olefin | 8/1 | 8/1 | 8/1 | 4/1 | 4/1 |
| Catalyst | AlCl₃ | AlCl₃ | AlCl₃ | AlCl₃ | AlCl₃ |
| Catalyst wt % | 0.88 | 0.79 | 0.79 | 1.1 | 1 |
| Reaction Temperature | 40 | 40 | 40 | 40 | 40 |
| Reaction Time, hrs | 24 | 24 | 24 | 24 | 24 |
| Lube Yield, wt % | 75 | 91 | 85 | 80 | 100 |
| Lube Properties: | | | | | |
| V100° C., cS | 4.87 | 5.08 | 4.90 | 5.53 | 8.35 |

TABLE 6-continued

Ar-PAO from Dimers of Mixed 1-C8, C10 and C12 Olefins with Aromatics

| Example | 17 | 18 | 19 | 20 | 21 |
|---|---|---|---|---|---|
| V40° C., cS | 26.94 | 30.11 | 28.69 | 35.42 | 74.46 |
| VI | 102 | 94 | 90 | 89 | 75 |
| Br. No | 1.5 | | | | |
| Pour Point, °C. | <−38 | <−42 | <−40 | <−43 | <−42 |
| DSC IP time, min. At 500 psi, 165° C. | 48 min. | 51 min. | 46 | 41 | |

Example 22–23

Toluene-PAO Used in an Industrial Oil Formulation

The Ar-PAO made from toluene and 1-dodecene was used in a synthetic circulation oil formulation. The resulting oil was clear without precipitate and excellent viscometrics and oxidative stability, as shown below in Table 7:

TABLE 7

Properties of a Synthetic Circulation Oil made with Ar-PAO from toluene and 1-dodecene

| Example | 22 | 23 |
|---|---|---|
| Wt % Ar-PAO in synthetic circulation oil formulation | 25 tol-C24 | 25 tol-C28 |
| Appearance | clear | clear |
| V100° C., cS | 53.94 | 51.62 |
| Vi | 151 | 158 |
| B10 325° C./40 hrs: | | |
| % Visc. Increase | — | 1.0 |
| Sludge | — | nil |
| TAN | — | 0.5 |

Example 24

Ar-PAO from Olefin Dimers

Polyalphalolefins (PAO) Rich in dimer contents were prepared from decene, dodecene, or tetradecene, or $C_8$ to $C_{12}$ mixed olefins. Isomerized $C_{20}$–$C_{24}$ olefins were produced by reacting a solid Gulftene 2024 (available from Chevron Chem. Co.) at 200° C. with 0.3 wt % calcined zeolite beta catalyst.

The alkylation reaction was carried out by mixing proper amount of PAO, aromatic component and powder $AlCl_3$ catalyst or pressurized with $BF_3$ catalyst. The mixture was heated to reaction temperature overnight. The reaction was quenched with 5% NaOH and washed with de-ionized water. The lube product was isolated by distillation at 150° C./10 millitorr for two hours.

Example 25

Preparation of Ar-PAO from Olefin Dimers with Benzene or Toulene

Tables 9 and 10 summarize the lube yields and viscometrics of the products prepared by reacting the dimers of 1-decene, 1-dodecene, 1-tetradecene or mixed $C_{8,10,12}$ alpha-olefins with benzene or toluene.

TABLE 9

Ar-PAO from Benzene and α-Olefin Dimers

| α-Olefin Type | decene | dodecene | tetra-decene | $C_{8,10,12}$ mixture | — |
|---|---|---|---|---|---|
| Dimer Composition | $C_{20}H_{40}$ | $C_{24}C_{48}$ | $C_{28}H_{58}$ | $C_{16}$–$C_{24}$ (av. $C_{20}$) | isomerized $C_{20}$–$C_{24}$) (b) |
| Molar Ratio of Bz/Dimer | 8/1 | 8/1 | 8/1 | 8/1 | 8/1 |
| Lube Yield, wt % | 59 | 93 | 83 | 75 | 86 |
| Lube Properties: | | | | | |
| Visc. 100° C., cS | 4.52 | 5.63 | 6.58 | 4.87 | 4.64 |
| Visc. @ 40° C., cS | 25.2 | 33.38 | 40.43 | 26.94 | 20.76 |
| VI | 82 | 107 | 116 | 102 | 146 |
| Pour Point, °C. | na | <−45 | <−45 | <−40 | +15 |
| Bromine No. | 4.6 | 0.3 | na | 1.5 | 1 |
| DSC Induction Time, min. (a) | — | 52 | 55 | 48 | — |

(a) DSC conditions: 165° C., 500 psi oxygen pressure
(b) Prepared by isomerizing Gulftene 2024 wax at 200° C. using zeolite beta catalyst

TABLE 10

Ar-PAO from Toluene and α-Olefin Dimers

| α-Olefin Type | dodecene | tetradecene | $C_{8,10,12}$ mixture | isomerized |
|---|---|---|---|---|
| Dimer Composition | $C_{24}H_{48}$ | $C_{28}H_{56}$ | $C_{16}$–$C_{24}$ (av. $C_{20}$) | $C_{20}$–$C_{24}$ (b) |
| Molar Ratio of BZ/Dimer | 8/1 | 8/1 | 8/1 | 8/1 |
| Lube Yield, wt % | 89 | 92 | 91 | 95 |
| Lube Properties: | | | | |
| 100° C. Visc., cS | 5.83 | 6.58 | 5.08 | 5.16 |
| 40° C. Visc., cS | 37.44 | 42.99 | 30.11 | 27.63 |
| VI | 95 | 1o5 | 94 | 118 |
| Pour Point, °C. | <−35 | <−43 | <−42 | 0 |
| DSC Induction Time, min. (a) | 49 | 52 | 51 | +2 |

(a) DSC conditions: 165° C. m 500 psi oxygen pressure
(b) Prepared by isomerizing Gulftene 2024 wax at 200° C. using zeolite beta catalyst It can be seen from Table 9 and Table 10 that the Ar-PAOs were produced in >90% yields using less than 1 wt % $AlCl_3$ catalyst.

Figure 3:
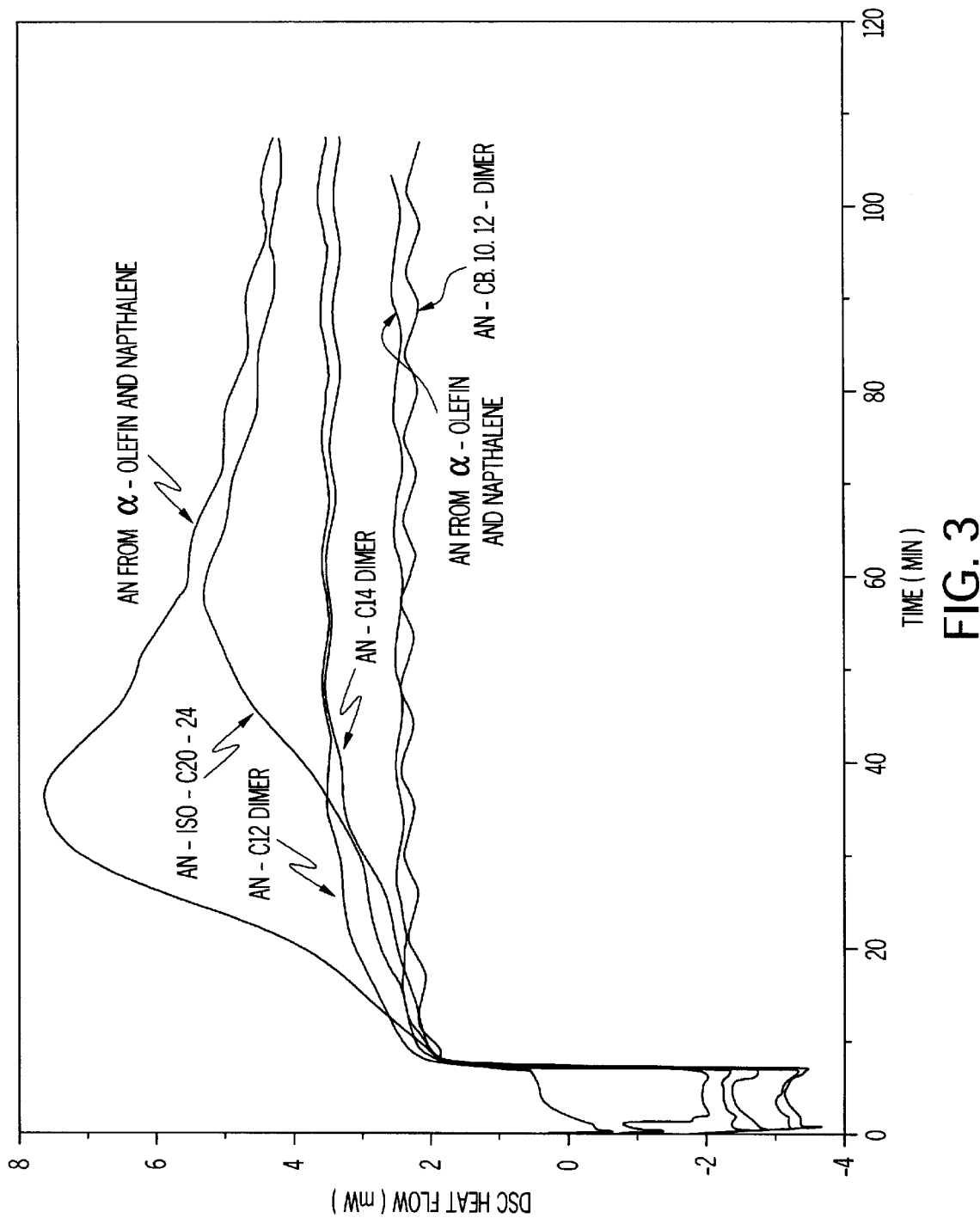
FIG. 3 is a differential scanning calorimetry plot showing that the alkylated naphthalene based on α-olefin dimers have better oxidative stability than the high viscosity alkylnaphthalene produced from simple α-olefin and naphthalene.

The Ar-PAOs have excellent viscometrics; i.e., low pour points (<−40° C.) and good VI. The Ar-PAOs made from benzene were found to have slightly higher VI than Ar-PAOs made from toluene or xylenes. FIG. 3 is a plot of VI versus Viscosity for Ar-PAOs listed in Tables 9 and 10. It can be seen that The presence of the extra methyl group on the benzene ring decreased the lube VI.

The bromine numbers of the lube products were generally low, <2 (Table 9), indicating that the lube products were fully saturated and no further hydrofinishing was needed.

The oxidative stabilities of Ar-PAO were excellent as indicated by long DSC induction time at 165° C. and 500 psi oxygen atmosphere: 50 minutes for Ar-PAO vs. 25 minutes for dibasic ester or 36 minutes for PAO.

Example 26

Alkylnaphthalene (AN) Base Stock from Olefin Dimers and Naphthalene

Alkylnaphthalene (AN) base stock has superior thermal, oxidative and hydrolytic stability. In some applications, a thick AN fluid would be desirable. It was found that a 9–12 cS AN could be produced using α-olefin dimers as starting material. Table 11 summarizes the lube yields and viscometrics of the products prepared by reacting naphthalene with the dimers of 1-decene, 1-dodecene, 1-tetradecene or mixed $C_{8,10,12}$ 1-olefins or with isomerized $C_{20}$–$C_{24}$ olefins. All the AN fluids from the α-olefin dimers have very low pour points (<−40° C.) and good viscometrics. FIG. 4 shows differential scanning calorimetry data indicating that the ANs based on α-olefin dimers have better oxidative stability than the high viscosity AN produced from simple α-olefin and naphthalene.

TABLE 11

Ar-PAO from Naphthalene and α-Olefin Dimers

| Dimer Composition | $C_{20}H_{40}$ | $C_{24}H_{48}$ | $C_{28}H_{56}$ | $C_{15}$–$C_{24}$ (avg. $C_{20}$) | isomerized $C_{20}$–$C_{24}$ (b) |
|---|---|---|---|---|---|
| Molar Ratio Aromatic/Olefin | 4/1 | 4/1 | 4/1 | 4/1 | 4/1 |
| Lube Yields, wt % | 32.7 | 100 | 93.1 | 100 | 98.3 |
| Lube Properties: | | | | | |
| 100° C. Visc., cS | 5.45 | 11.03 | 11.82 | 8.35 | 8.01 |
| 40° C. Visc., cS | 38.7 | 114.1 | 118.93 | 74.46 | 56.38 |
| VI | 62 | 77 | 85 | 75 | 109 |
| Pour Point, ° C. | na | <−40 | <−42 | <−42 | 0.7 |

(b) Prepared by isomerizing Gulftene 2024 wax at 200° C. using beta catalyst.

Example 27

Arylated Base Stocks From Isomerized $C_{20}$–$C_{24}$ Olefins

The synthesis and properties of the arylated linear internal olefins of $C_{20}$ to $C_{24}$ range were determined. The linear, internal $C_{20-24}$ internal olefins differ from α-olefin dimers. The isomerized α-olefins have completely linear structure, whereas the α-olefin dimers have slight branching and the double bonds are located in the middle of the molecules. As a result, the arylated products from these isomerized $C_{20}$–$C_{24}$ olefins (Table 9, 10 and 11) were found to be inferior to the Ar-PAO from olefin dimers (Table 1, 2 and 4; FIG. 4). For example, the arylated base stocks from isomerized $C_{20}$–$C_{24}$ olefins have very high pour points (0–+15° C.), which are not as good as arylated PAO. The oxidative stability of AN from isomerized $C_{20}$–$C_{24}$ olefins is also inferior to AN from olefin dimers (See FIG. 4).

It is intended that each of the patents, applications, and printed publications mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A method for the preparation of arylated poly α-olefins comprising the steps of:
    (a) oligomerizing one or more α-olefins in the presence of an acid catalyst to form olefin dimers and higher oligomers; and
    (b) arylating the olefin oligomers with an aromatic compound in the presence of the same catalyst to form the arylated poly alpha olefins.

2. The method of claim 1 wherein the catalyst is promoted $BF_3$, $AlCl_{31}$ triflic acid, $BCl_3$ or $AlBr_3$.

3. The method of claim 1, wherein the acid catalyst is an acidic zeolite.

4. The method of claim 1 wherein the α-olefins have from about 8 to about 14 carbon atoms.

5. The method of claim 4 wherein the α-olefins have from about 10 to about 14 carbon atoms.

6. The method of claim 5 wherein the α-olefins have from about 10 to about 12 carbon atoms.

7. The method of claim 6 wherein the aromatic compound is benzene, an alkyl-benzene, naphthalene or an alkyl naphthalene.

8. The method of claim 7 wherein the aromatic compound is toluene, 0-, m- or p-xylene, naphthalene, or a mixture thereof.

9. The method of claim 1 wherein the ratio of aromatic compound to olefin oligomer is from about 0.5:1 to about 8:1.

10. The method of claim 1 wherein the ratio of aromatic compound to olefin oligomer is from about 1:1 to about 8:1.

* * * * *